(12) United States Patent
Irie

(10) Patent No.: US 9,173,636 B2
(45) Date of Patent: Nov. 3, 2015

(54) ULTRASOUND PROBE

(71) Applicant: OLYMPUS CORPORATION, Tokyo (JP)

(72) Inventor: Kei Irie, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/768,405

(22) Filed: Feb. 15, 2013

(65) Prior Publication Data

US 2013/0204140 A1    Aug. 8, 2013

Related U.S. Application Data

(63) Continuation of application No. PCT/JP2012/076272, filed on Oct. 11, 2012.

(30) Foreign Application Priority Data

Nov. 24, 2011  (JP) .................................. 2011-256430

(51) Int. Cl.
*A61B 8/00* (2006.01)
*A61B 8/12* (2006.01)
*A61B 1/00* (2006.01)

(52) U.S. Cl.
CPC ............. *A61B 8/4444* (2013.01); *A61B 1/0011* (2013.01); *A61B 8/12* (2013.01); *A61B 8/445* (2013.01); *A61B 1/00114* (2013.01)

(58) Field of Classification Search
None
See application file for complete search history.

(56) References Cited

U.S. PATENT DOCUMENTS

| 4,815,471 | A | * | 3/1989 | Stobie | ........................ 600/488 |
| 5,176,140 | A | | 1/1993 | Kami et al. | |
| 6,017,311 | A | * | 1/2000 | Sakamoto | ..................... 600/459 |
| 2008/0119738 | A1 | * | 5/2008 | Imahashi et al. | .............. 600/462 |

FOREIGN PATENT DOCUMENTS

| EP | 1 849 414 A1 | 10/2007 |
| JP | 2005-237611 | 9/2005 |
| JP | 2009-028109 | 2/2009 |

OTHER PUBLICATIONS

Extended Supplementary Search Report dated Oct. 28, 2013 from related European Application No. 12 85 1965.9.

* cited by examiner

*Primary Examiner* — Unsu Jung
*Assistant Examiner* — Serkan Akar
(74) *Attorney, Agent, or Firm* — Scully, Scott, Murphy & Presser, PC

(57) ABSTRACT

An ultrasound probe including: an ultrasound transmission/reception portion; a cable; a housing; a hole portion of the housing; an insulation pipe having a proximal end side exposed outside the housing; an insulation tube covering an outer circumference of an exposed region of the insulation pipe and an outer circumference of the cable; an adhesive located between the outer circumference of the exposed region and a distal end side region of the insulation tube and configured to adhere the insulation pipe and the insulation tube to each other; and a sticky member disposed between the exposed region and the distal end side region together with the adhesive.

9 Claims, 7 Drawing Sheets

ULTRASOUND PROBE

CROSS REFERENCE TO RELATED APPLICATION

This application is a continuation application of PCT/JP2012/076272 filed on Oct. 11, 2012 and claims benefit of Japanese Application No. 2011-256430 filed in Japan on Nov. 24, 2011, the entire contents of which are incorporated herein by this reference.

BACKGROUND OF THE INVENTION

1. Field of the Invention

The present invention relates to an ultrasound probe provided with an ultrasound transmission/reception portion having an ultrasound transmitting/receiving surface configured to transmit and receive ultrasound and a cable having a distal end electrically connected to the ultrasound transmission/reception portion.

2. Description of the Related Art

An ultrasound probe used for obtaining an ultrasound image by transmitting and receiving ultrasound to and from a region to be examined is configured such that an ultrasound transmission/reception portion, which is located at a distal end of the ultrasound probe and which is configured to transmit and receive ultrasound, is connected, through a cable, to a connector which is located at a proximal end of the ultrasound probe and which connects the ultrasound probe to an ultrasound observation apparatus.

In addition, the ultrasound probe has a configuration in which the outer circumference of the cable is covered with an insulation tube, or the like, which is a reinforced insulation member, in order to ensure electrical safety of the cable.

Japanese Patent Application Laid-Open Publication No. 2009-28109 discloses a configuration in which an ultrasound transmission/reception portion to which a distal end of a cable is electrically connected is provided in a housing having an insulation property on a distal end side of an ultrasound probe, an insulation pipe through which the cable is inserted is fixed in a hole portion which is formed on the housing and from which the cable is extended outside the housing, and a distal end side region of an insulation tube is adhered and fixed with adhesive to an outer circumference of an exposed region of the insulation pipe which is exposed outside the housing.

SUMMARY OF THE INVENTION

An ultrasound probe according to one aspect of the present invention includes: an ultrasound transmission/reception portion having an ultrasound transmission/reception surface for transmitting and receiving ultrasound; a cable having a distal end electrically connected to the ultrasound transmission/reception portion; a housing configured to hold the ultrasound transmission/reception portion such that the ultrasound transmission/reception surface is exposed; a hole portion provided to the housing and configured to lead out the cable from inside of the housing; an insulation pipe through which the cable is inserted, the insulation pipe having a distal end side fixed to the hole portion in a state of contacting an inner circumference of the hole portion, and a proximal end side exposed outside the housing; an insulation tube configured to cover an outer circumference of an exposed region of the insulation pipe which is exposed from the hole portion and an outer circumference of the cable led out from a proximal end of the insulation pipe; an adhesive located between the outer circumference of the exposed region of the insulation pipe and a distal end side region of the insulation tube covering the outer circumference of the exposed region, and configured to adhere the insulation pipe and the insulation tube to each other; and a liquid dripping prevention portion disposed between the exposed region of the insulation pipe and the distal end side region of the insulation tube, together with the adhesive, the liquid dripping prevention portion being configured to prevent the adhesive from flowing out from the proximal end of the insulation pipe and contacting the cable.

DETAILED DESCRIPTION OF THE PREFERRED EMBODIMENT(S)

Hereinafter, embodiments of the present invention will be described with reference to drawings. Note that each of the drawings is a pattern diagram, and care should be taken to the fact that the relationship between the thicknesses and widths of the respective members, a ratio of the thickness of a certain member to that of another member, and the like are different from those of the members in actual sizes. It is needless to say that each of the drawings includes a relationship and a ratio of the dimensions which are different from those in other drawings.

First Embodiment

Figure 1:
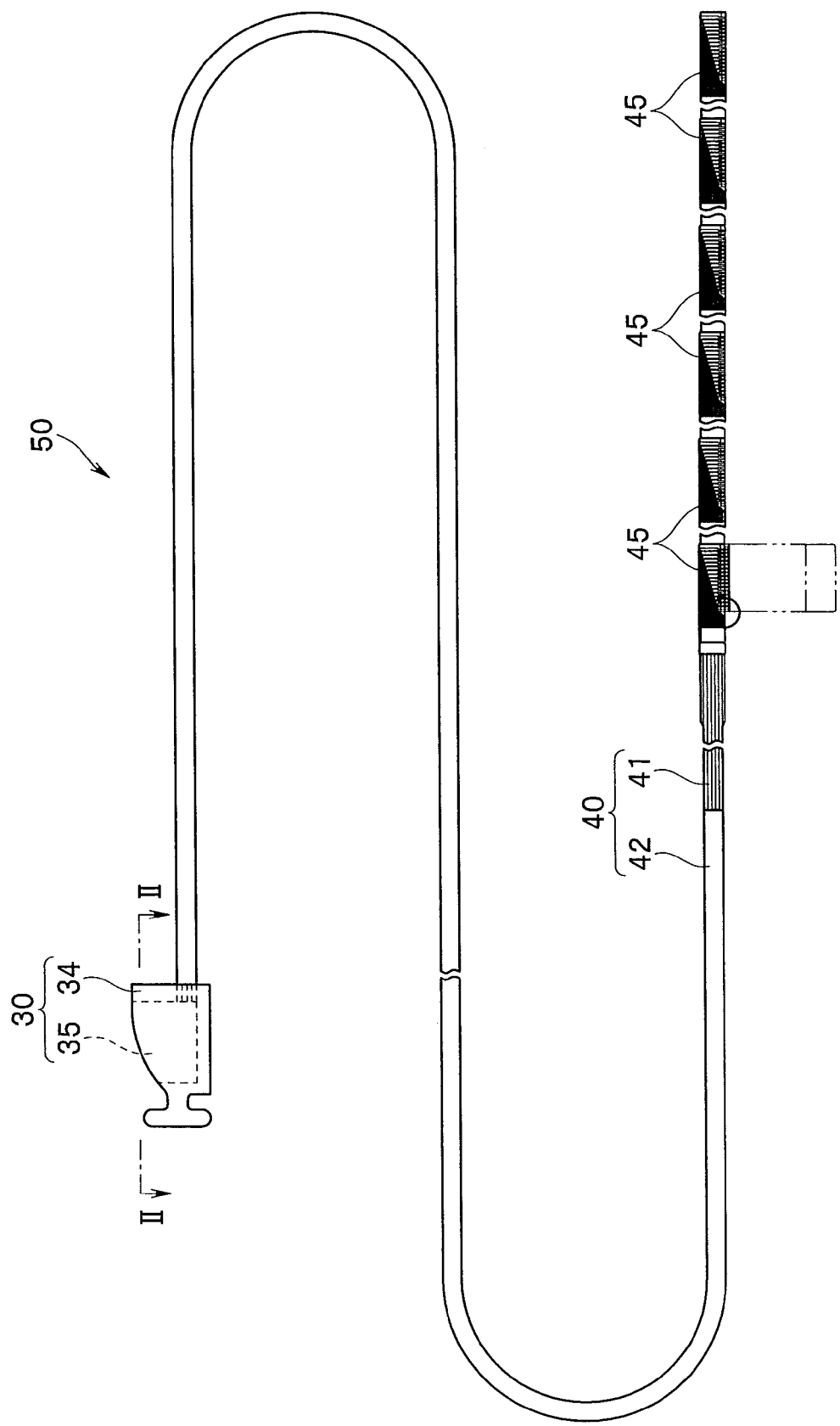
FIG. 1 is a perspective view showing an ultrasound probe according to a first embodiment.
Figure 2:
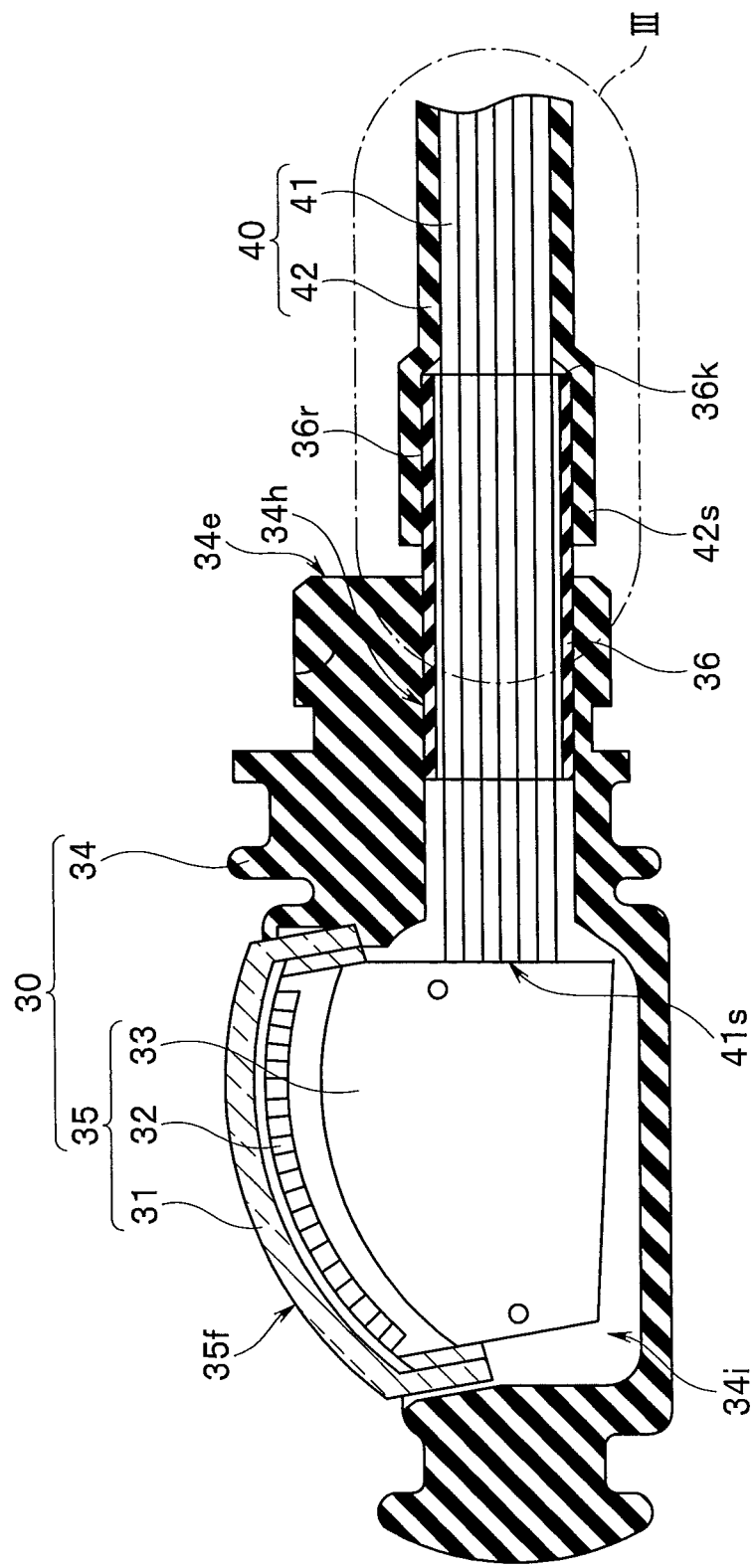
FIG. 2 is a cross-sectional view of the ultrasound probe along the II-II line in FIG. 1.
Figure 3:
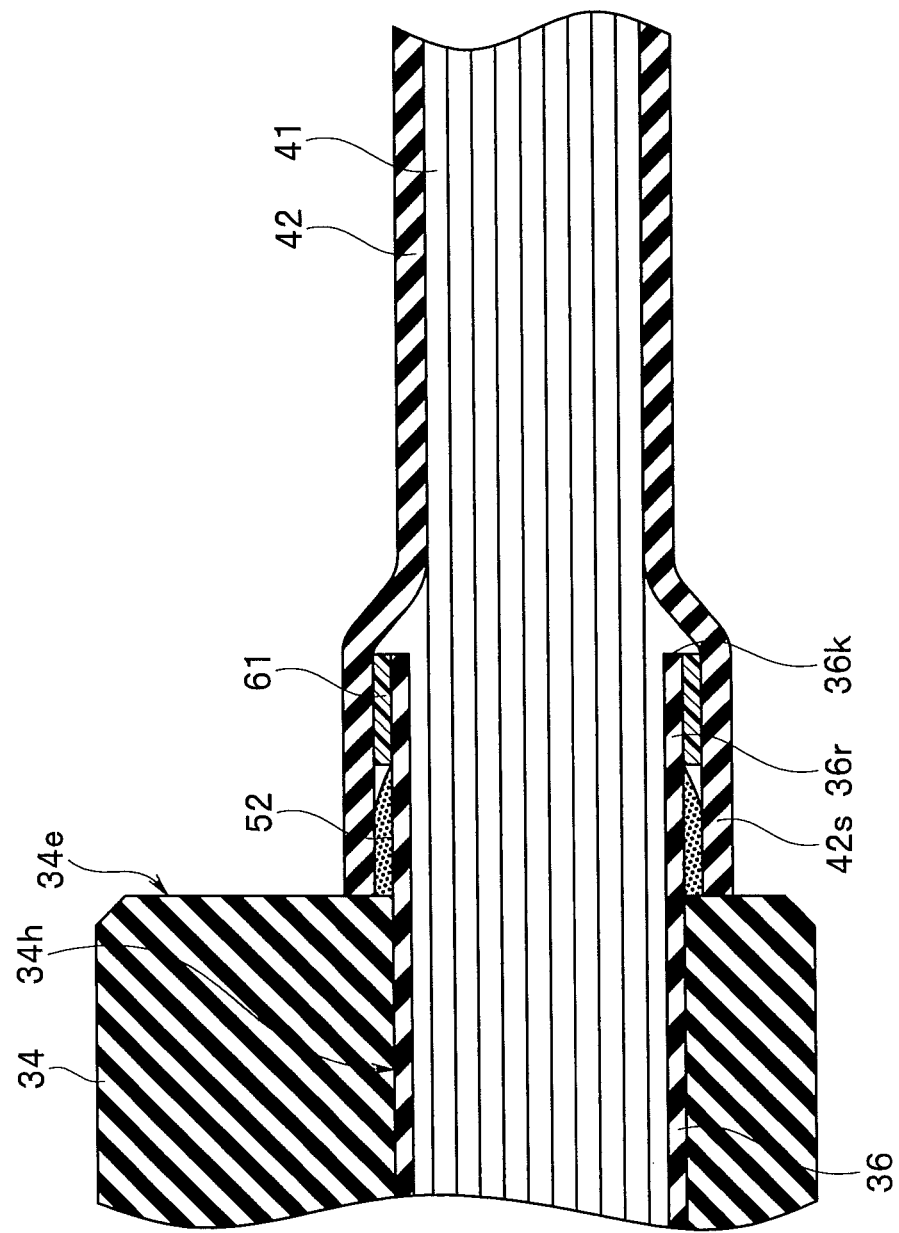
FIG. 3 is an enlarged cross-sectional view of the region of the ultrasound probe enclosed by the line III in FIG. 2.

FIG. 1 is a perspective view showing an ultrasound probe according to the present embodiment, FIG. 2 is a cross-sectional view of the ultrasound probe along the II-II line in FIG. 1, and FIG. 3 is an enlarged cross-sectional view of the region of the ultrasound probe enclosed by the line III in FIG. 2.

As shown in FIG. 1, an ultrasound probe 50 includes an ultrasound transducer cable 40. The ultrasound transducer cable 40 has a main part configured by a cable 41 including a plurality of signal lines, and an insulation tube 42 which covers an outer circumference of the cable 41. In addition, the cable 41 including a plurality of signal lines is bundled into one with the insulation tube 42.

Figure 7:
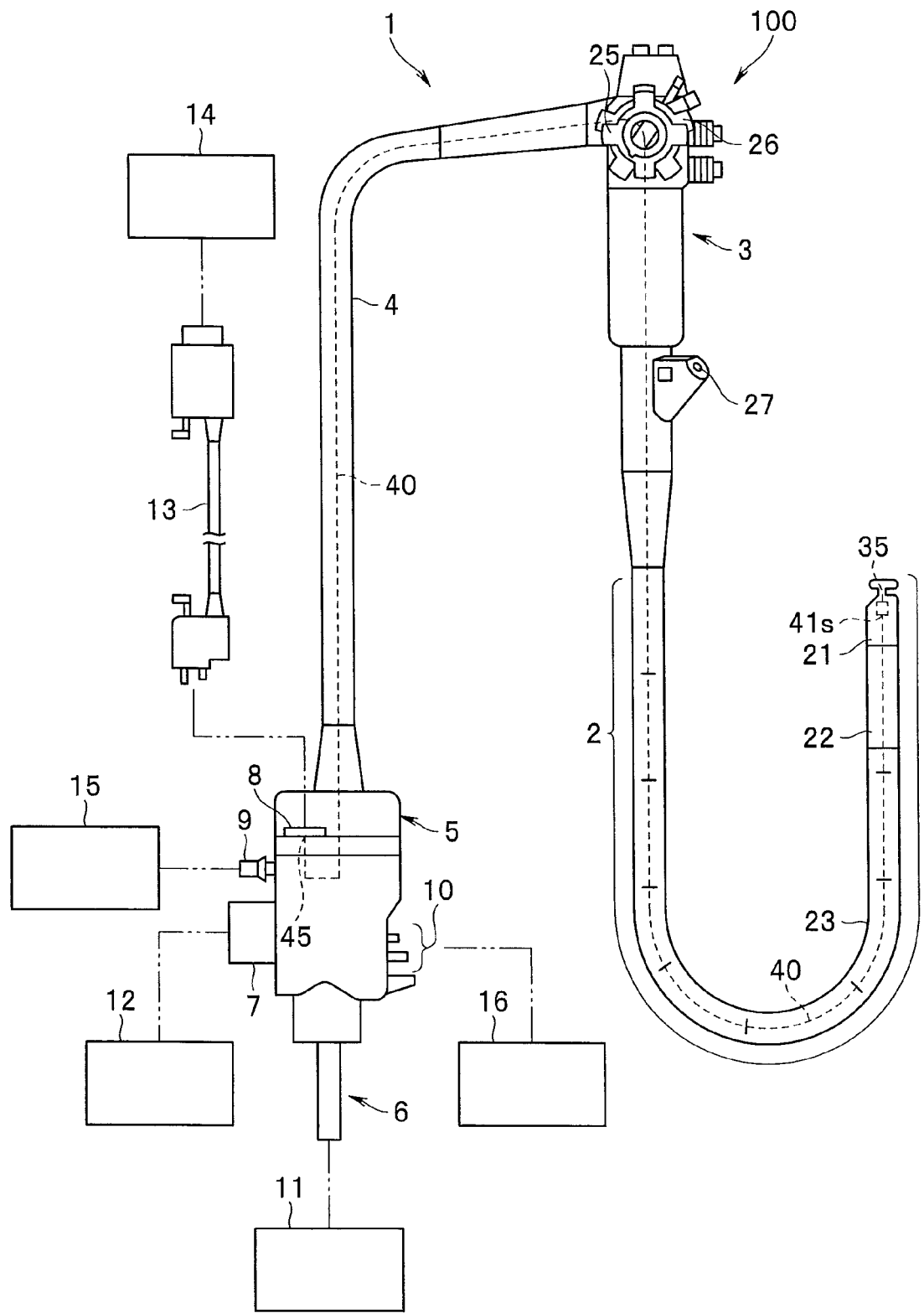
FIG. 7 is a view showing an ultrasound endoscope apparatus provided with an ultrasound endoscope including an ultrasound probe.

Note that the insulation tube 42 is made of a heat-shrinkable tube, for example, which is formed by a thin and flexible rubber or the like having voltage endurance, so as to ensure specified voltage endurance of the cable 41, and so as not to impede the flexibility of an insertion portion 2 when an ultrasound probe 50 is provided in an ultrasound endoscope 1 (Regarding these components, see FIG. 7).

Further, the insulation tube 42 has a function for preventing the cable 41 from contacting metal members such as a light guide, a balloon conduit, and a forceps channel and the like, not shown, provided in the insertion portion 2, when the ultrasound probe 50 is provided in the ultrasound endoscope 1, to be described later, for example. That is, the insulation tube 42 has a function for insulating the cable 41 from other metal members.

In addition, since the outer circumference of the cable 41 is not covered with the insulation tube 42 on the proximal end side of the ultrasound transducer cable 40, the cable 41 is exposed. Furthermore, a plurality of connectors 45, which electrically connect the cable 41 to a substrate, not shown, of an ultrasound connector 8 provided in an endoscope connector 5 to be described later, are provided to the exposed region of the cable 41 (regarding these components, see FIG. 7).

Furthermore, the distal end of the ultrasound transducer cable 40 is connected with an ultrasound transducer unit 30.

As shown in FIG. 2, the ultrasound transducer unit 30 has a main part configured by including an ultrasound transmission/reception portion 35 having an ultrasound transmission/reception surface 35*f* configured to transmit and receive ultrasound, and a housing 34 configured to hold the ultrasound transmission/reception portion 35 such that the ultrasound transmission/reception surface 35*f* is exposed.

Note that, similarly as the insulation tube 42, the housing 34 is made of a member having voltage endurance, for example, a resin such as polysulphone, polyimide, or PET, in order to ensure specified voltage endurance of the cable 41.

The ultrasound transmission/reception portion 35 includes an ultrasound transducer 32, an acoustic lens 31, and a substrate 33, and is disposed in a space 34*i* located on a distal end side in the housing 34.

The ultrasound transducer 32 emits ultrasound to a region to be examined through the acoustic lens 31, and after the emission, receives ultrasound reflected back from the region to be examined through the acoustic lens 31 to convert the ultrasound into an electric signal.

The acoustic lens 31 has a function for collecting the ultrasound emitted from the ultrasound transducer 32 to the region to be examined so as not to diffuse, and emitting the ultrasound. Note that the surface of the acoustic lens 31 configures the ultrasound transmission/reception surface 35*f*.

The substrate 33 is electrically connected to the ultrasound transducer 32, and is connected with a distal end 41*s* of the cable 41, which is not covered with the insulation tube 42, on the distal end side of the ultrasound transducer cable 40.

According to such a configuration, the electric signal converted from the ultrasound by the ultrasound transducer 32 is transmitted to the ultrasound transducer cable 40 through the substrate 33.

In addition, as shown in FIGS. 2 and 3, a hole portion 34*h* for leading out the cable 41 having the distal end electrically connected to the substrate 33, from inside of the housing 34 to the outside of the housing 34, is formed on the proximal end side of the housing 34, and the hole portion 34*h* is formed such that the space 34*i* inside the housing 34, in which the ultrasound transmission/reception portion 35 is provided, communicates with the proximal end surface 34*e* of the housing 34.

A distal end side of the insulation pipe 36 through which the cable 41 is inserted is fixed to the hole portion 34*h* so as to contact the inner circumference of the hole portion 34*h*. Note that the proximal end side of the insulation pipe 36 is located so as to be exposed outside the housing 34.

In addition, similarly as the insulation tube 42 and the housing 34, the insulation pipe 36 is made of a member having voltage endurance, for example, a resin such as polysulphone, polyimide, or PET, and has a function for preventing other metal members from contacting the cable 41, in order to ensure specified voltage endurance of the cable 41.

Note that, since other configurations of the ultrasound transducer unit 30 are the same as those of a well-known ultrasound transducer unit, the description thereof will be omitted.

The distal end side region of the cable 41, more specifically, as shown in FIG. 2, a region of the cable 41 which is more distal end side than the region inserted into the insulation pipe 36 is not covered with the insulation tube 42. That is, the insulation tube 42 covers the outer circumference of the part of the cable 41 led out rearward from a proximal end 36*k* of the insulation pipe 36, except for the connectors 45 provided on the proximal end side.

In addition, a distal end side region 42*s* of the insulation tube 42 covers the outer circumference of an exposed region 36*r* of the insulation pipe 36, which is exposed from the hole portion 34*h*, and as shown in FIG. 3, the distal end side region 42*s* is adhered and fixed to the outer circumference of the exposed region 36*r* with an adhesive 52 applied to a distal end side area between the outer circumference of the exposed region 36*r* and the distal end side region 42*s*.

Note that, in order to improve the adherence property of the distal end side region 42*s* with respect to the exposed region 36*r*, the area where the adhesive 52 is applied on the outer circumference of the exposed region 36*r* may be so formed as to have a rough surface.

In addition, as shown in FIG. 3, a sticky member 61, which is a liquid dripping prevention portion that prevents the adhesive 52 from flowing into the insulation tube 42 from the proximal end 36*k* of the insulation pipe 36 and contacting the cable 41, is provided between the outer circumference of the exposed region 36*r* and the distal end side region 42*s* so as to be located at an area which is more proximal end side than the area where the adhesive 52 is applied.

The sticky member 61 clings to the outer circumference of the exposed region 36*r* and the distal end side region 42*s*, and is made of a member having a higher viscosity than the adhesive 52, for example, a member having a viscosity of 2 to 30 N, such as a double-stick tape made of silicone.

Note that the sticky member 61 just clings to the distal end side region 42*s*. Therefore, the distal end side region 42*s* is not damaged by the clinging of the sticky member 61.

Since other configurations of the ultrasound probe 50 are the same as those of a known ultrasound probe, the description thereof will be omitted.

Thus, in the present embodiment, the distal end side region 42*s* of the insulation tube 42 is adhered and fixed to the outer circumference of the exposed region 36*r* of the insulation pipe 36 with the adhesive 52, and the sticky member 61 is provided between the outer circumference of the exposed region 36*r* and the distal end side region 42*s* so as to be located at the area which is more proximal end side than the area where the adhesive 52 is applied.

According to such a configuration, since the sticky member 61 clings to the outer circumference of the exposed region 36*r* and the distal end side region 42*s*, there is no gap in a proximal end side area between the outer circumference of the exposed region 36*r* and the distal end side region 42*s*. Therefore, it is possible to surely prevent the adhesive 52 from flowing into the insulation tube 42 from the proximal end 36k of the insulation pipe 36 by the sticky member 61.

In addition, the insulation tube 42 and the insulation pipe 36 which cover the outer circumference of the cable 41 are made of the members having voltage endurance, thereby capable of sufficiently ensuring specified voltage endurance of the cable 41.

As described above, it is possible to provide the ultrasound probe 50 having a configuration capable of preventing the adhesive 52, which fixes the distal end side region 42s of the insulation tube 42 to the outer circumference of the exposed region 36r of the insulation pipe 36, from flowing out without increasing the length of the exposed region 36r while surely ensuring the electric safety of the cable 41 using the insulation pipe 36 and the insulation tube 42.

Second Embodiment

Figure 4:
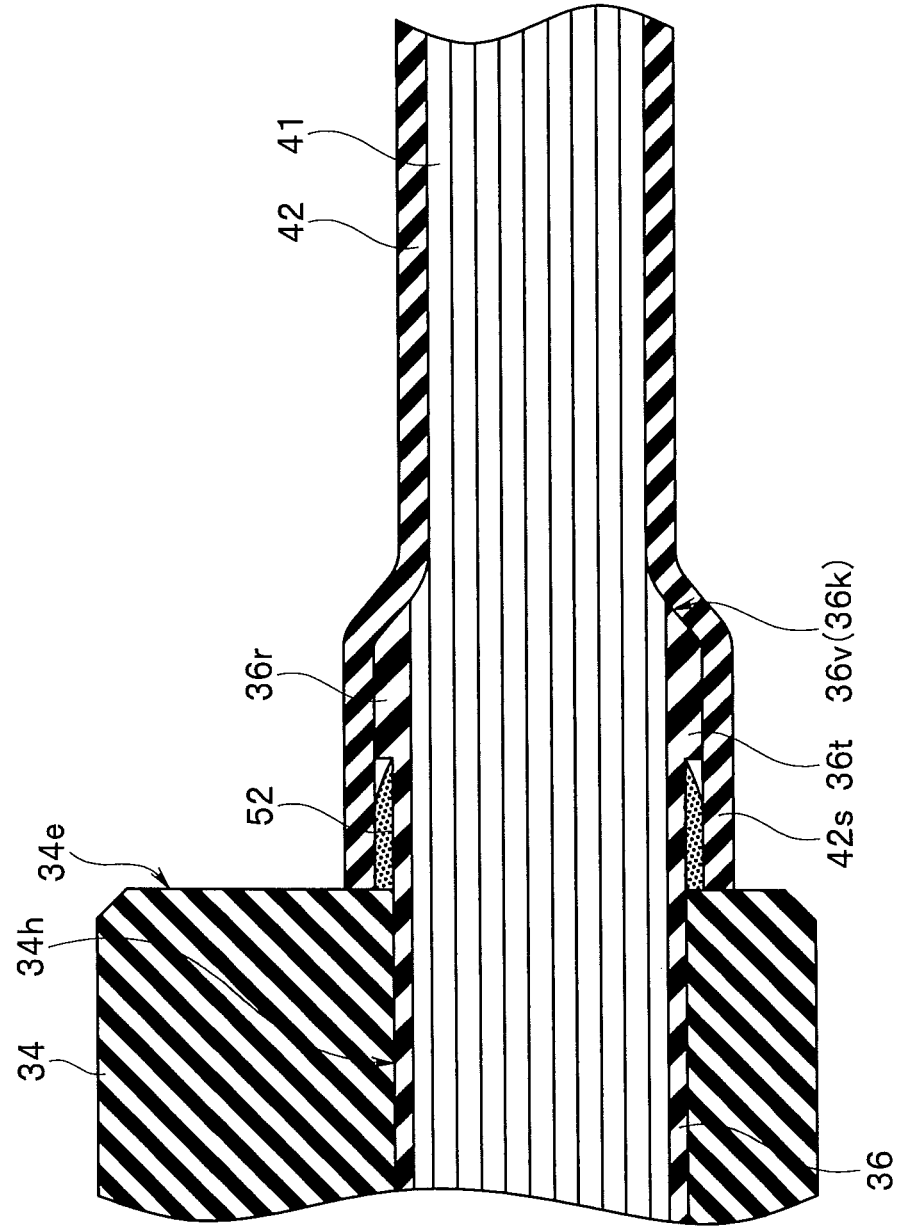
FIG. 4 is a partial cross-sectional view showing, in an enlarged manner, a vicinity of a proximal end side of an insulation pipe of an ultrasound probe according to a second embodiment.

FIG. 4 is a partial cross-sectional view showing, in an enlarged manner, the vicinity of the proximal end side of the insulation pipe of the ultrasound probe according to the present embodiment.

The configuration of the ultrasound probe according to the second embodiment is different from that of the ultrasound probe according to the first embodiment shown in the above-described FIGS. 1 to 3 in that, instead of the sticky member, a projection portion, which is provided along the outer circumference of the proximal end of the insulation pipe, is used for the liquid dripping prevention portion. Accordingly, the same components as those in the first embodiment are attached with the same reference numerals and the description thereof will be omitted.

As shown in FIG. 4, in the present embodiment, an outward flange-shaped projection portion 36t as a liquid dripping prevention portion is formed in a circumferential shape along the outer circumference of the proximal end of the exposed region 36r of the insulation pipe 36.

The projection portion 36t is provided between the outer circumference of the exposed region 36r and the distal end side region 42s so as to be located in the area which is more proximal end side than the area where the adhesive 52 is applied, and contacts the distal end side region 42s of the insulation tube 42.

Note that the projection portion 36t may be formed as a body separated from the insulation pipe 36, or may be formed integrally with the insulation pipe 36 by causing the outer circumference of the proximal end of the insulation pipe 36 to be bulged.

In addition, also in the present embodiment, the distal end side region 42s of the insulation tube 42 covers the outer circumference of the exposed region 36r of the insulation pipe 36 and is adhered and fixed to the outer circumference of the exposed region 36r with the adhesive 52 applied between the outer circumference of the area, which is more distal end side than the projection portion 36t, of the exposed region 36r and the distal end side region 42s.

The projection portion 36t is provided between the outer circumference of the exposed region 36r and the distal end side region 42s so as to be located on the more distal end side than the area where the adhesive 52 is applied, and blocks the adhesive 52 which attempts to flow out toward the proximal end side, thereby preventing the adhesive 52 from flowing into the insulation tube 42 from the proximal end 36k of the insulation pipe 36 and contacting the cable 41.

Note that a tapered surface 36v, which inclines toward the cable 41 side from the outer circumference to the inner circumference of the insulation pipe 36, is formed at the proximal end 36k of the insulation pipe 36.

The tapered surface 36v is formed by cutting off an edge portion of the end face of the outer circumference of the proximal end 36k of the insulation pipe 36, in order to prevent damage on the insulation tube 42 by the edge portion of the end face.

Note that other configurations of the ultrasound probe 50 are the same as those in the above-described first embodiment.

Thus, in the present embodiment, the distal end side region 42s of the insulation tube 42 is adhered and fixed to the outer circumference of the exposed region 36r of the insulation pipe 36 with the adhesive 52. In addition, the projection portion 36t formed in a circumferential shape along the outer circumference of the proximal end of the insulation pipe 36 is provided between the outer circumference of the exposed region 36r and the distal end side region 42s so as to be located in the area which is more proximal end side than the area where the adhesive 52 is applied.

According to such a configuration, the projection portion 36t blocks the adhesive 52 flowing out toward the proximal end side on the outer circumference of the exposed region 36r, thereby capable of surely preventing the adhesive 52 from flowing into the insulation tube 42 from the proximal end 36k of the insulation pipe 36.

Note that other effects are the same as those in the above-described first embodiment.

Third Embodiment

Figure 5:
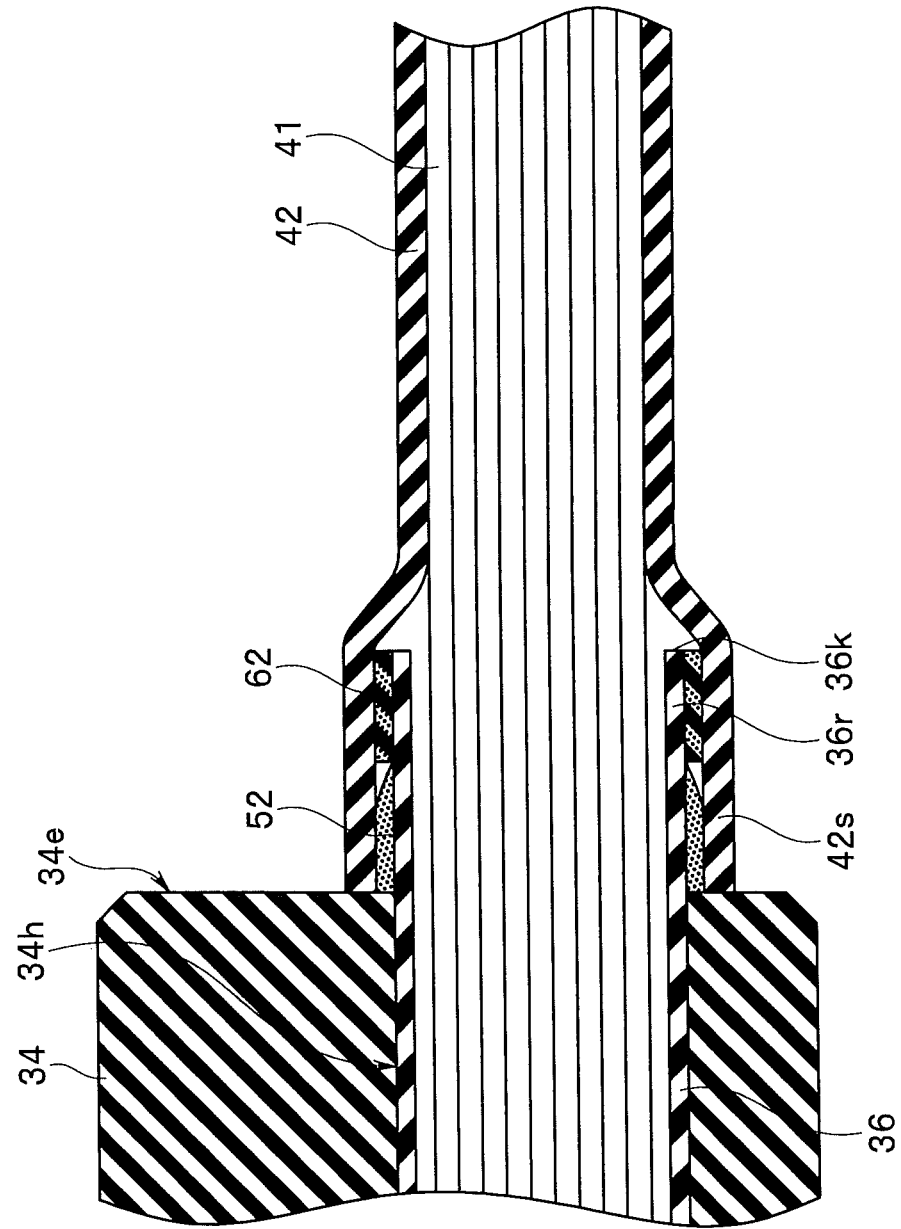
FIG. 5 is a partial cross-sectional view showing, in an enlarged manner, a vicinity of a proximal end side of an insulation pipe of an ultrasound probe according to a third embodiment.

FIG. 5 is a partial cross-sectional view showing, in an enlarged manner, the vicinity of the proximal end side of the insulation pipe of the ultrasound probe according to the present embodiment.

The configuration of the ultrasound probe according to the third embodiment is different from the ultrasound probe according to the first embodiment shown in the above-described FIGS. 1 to 3, in that an absorbing member is used for the liquid dripping prevention portion, instead of the sticky member. Accordingly, the components as those in the first embodiment are attached with the same reference numerals, and the description thereof will be omitted.

As shown in FIG. 5, in the present embodiment, an absorbing member 62 as the liquid dripping prevention portion is provided between the outer circumference of the exposed region 36r and the distal end side region 42s so as to be located in the area which is more proximal end side than the region where the adhesive 52 is applied.

The absorbing member 62 has a function for absorbing the adhesive 52 flown out toward the proximal end side between the outer circumference of the exposed region 36r and the distal end side region 42s, and is made of an adhesive absorbing sheet.

Note that the adhesive absorbing sheet is a sheet-like porous member which can absorb fluid, and more specifically, a sponge such as polyurethane or polystyrene, or superabsorbent polymer such as sodium polyacrylate is used.

In addition, also in the present embodiment, the distal end side region 42s of the insulation tube 42 covers the outer circumference of the exposed region 36r of the insulation pipe 36, and is adhered and fixed to the outer circumference of the exposed region 36r with the adhesive 52 applied between the outer circumference of the area, which is more distal end side than the absorbing member 62, of the exposed region 36r and the distal end side region 42s.

The absorbing member 62 is provided between the outer circumference of the exposed region 36r and the distal end side region 42s so as to be located on the more proximal end side than the area where the adhesive 52 is applied. The absorbing member absorbs the adhesive 52 which attempts to flow out toward the proximal end side on the outer circumference of the insulation pipe 36, thereby preventing the adhesive 52 from flowing into the insulation tube 42 from the proximal end 36k of the insulation pipe 36 and contacting the cable 41.

Since the absorbing member 62 is made of a flexible porous member, as described above, the absorbing member does not cause damage on the insulation tube 42 contacting the absorbing member.

Other configurations of the ultrasound probe 50 are the same as those in the above-described first embodiment.

Thus, in the present embodiment, the distal end side region 42s of the insulation tube 42 is adhered and fixed to the outer circumference of the exposed region 36r of the insulation pipe 36 with the adhesive 52, and the absorbing member 62 is provided between the outer circumference of the exposed region 36r and the distal end side region 42s so as to be located in the area which is more proximal end side than the area where the adhesive 52 is applied.

According to such a configuration, the absorbing member 62 absorbs the adhesive 52 flown out toward the proximal end side on the outer circumference of the exposed region 36r, thereby surely preventing the adhesive 52 from flowing into the insulation tube 42 from the proximal end 36k of the insulation pipe 36.

Note that other effects are the same as those in the first embodiment.

Fourth Embodiment

Figure 6:
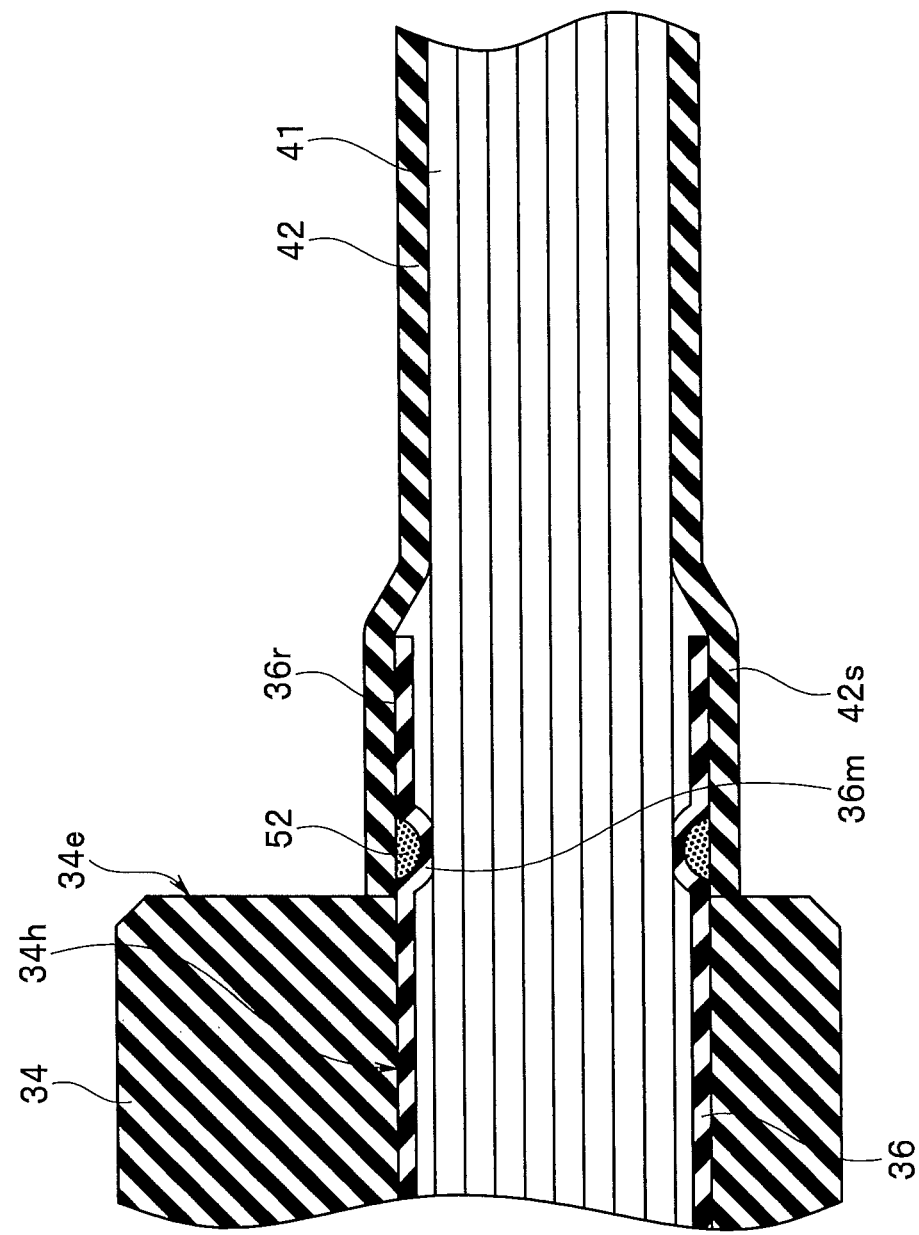
FIG. 6 is a partial cross-sectional view showing, in an enlarged manner, a vicinity of a proximal end side of an insulation pipe of an ultrasound probe according to a fourth embodiment.

FIG. 6 is a partial cross-sectional view showing, in an enlarged manner, the vicinity of the proximal end side of the insulation pipe of the ultrasound probe according to the present embodiment.

The configuration of the ultrasound probe according to the fourth embodiment is different from the ultrasound probe according to the first embodiment shown in the above-described FIGS. 1 to 3 in that a groove formed at the exposed region of the insulation pipe is used as the liquid dripping prevention portion, instead of the sticky member. Therefore, the same components as those in the first embodiment are attached with the same reference numerals and the description thereof will be omitted.

As shown in FIG. 6, in the present embodiment, a groove portion 36m as a liquid dripping prevention portion in which the adhesive 52 is injected is formed on the outer circumference of the exposed region 36r by causing the outer circumference to be dented.

Note that the groove portion 36m may be formed in a circumferential shape along the outer circumference of the exposed region 36r, or may be partially formed along the outer circumference. In addition, in FIG. 6, the groove portion 36m is formed on the exposed region 36r so as to be located in the vicinity of the proximal end surface 34e of the housing 34. However, the groove portion 36m may be formed at any position as along as the position is located on the exposed region 36r. Further, the groove portion 36m may be formed in plural numbers on the exposed region 36r so as to be located at positions separated from one another.

Furthermore, in the present embodiment, the distal end side region 42s of the insulation tube 42 directly covers the outer circumference of the exposed region 36r of the insulation pipe 36, and is adhered and fixed to the outer circumference of the exposed region 36r with the adhesive 52 injected in the groove portion 36m on the exposed region 36r.

The groove portion 36m prevents the adhesive 52 from flowing out toward the proximal end side on the outer circumference of the exposed region 36r by the adhesive 52 being injected in the groove portion between the outer circumference of the exposed region 36r and the distal end side region 42s, thereby preventing the adhesive 52 from flowing into the insulation tube 42 from the proximal end 36k of the insulation pipe 36 and contacting the cable 41.

Note that other configurations of the ultrasound probe 50 are the same as those in the above-described first embodiment.

Thus, in the present embodiment, the distal end side region 42s of the insulation tube 42 is adhered and fixed to the outer circumference of the exposed region 36r of the insulation pipe 36 with the adhesive 52, and the adhesive 52 is injected in the groove portion 36m formed on the outer circumference of the exposed region 36r.

According to such a configuration, extra adhesive 52 which is not used for adhering remains in the groove portion 36m. Therefore, it is possible to surely prevent the adhesive 52 from flowing into the insulation tube 42 from the proximal end 36k of the insulation pipe 36. Note that other effects are the same as those in the first embodiment.

The ultrasound probe 50 described above in the first to fourth embodiments are used in an ultrasound endoscope, for example.

FIG. 7 is a view showing an ultrasound endoscope apparatus provided with an ultrasound endoscope including an ultrasound probe.

As shown in FIG. 7, an ultrasound endoscope apparatus 100 includes a main part configured by an ultrasound endoscope 1, a light source device 11, a video processor 12, an ultrasound observation apparatus 14, a suctioning pump 15, and a water-feeding tank 16.

The ultrasound endoscope 1 includes a main part configured by an elongated insertion portion 2 configured to be inserted into a body, an operation portion 3 provided at a proximal end of the insertion portion 2 and serving also as a grasping portion, a flexible universal cord 4 extended from the operation portion 3, and an endoscope connector 5 provided at an extension end of the universal cord 4.

The endoscope connector 5 is provided with a light source connector 6, an electric connector 7, an ultrasound connector 8, a suction cap 9, and an air/water feeding mouthpiece 10.

The light source device 11 that supplies illumination light is configured to be attachable to and detachable from the light source connector 6. In addition, the video processor 12 that performs various signal processings is configured to be attachable to and detachable from the electric connector 7 through a signal cable, not shown.

Furthermore, as described above, the ultrasound observation apparatus 14 is configured to be attachable to and detachable from the ultrasound connector 8, through an ultrasound cable 13, the ultrasound connector 8 being electrically connected with the connectors 45 provided on the proximal end side of the cable 41 of the ultrasound transducer cable 40 (regarding these components, see FIG. 1).

In addition, the suctioning pump 15 is configured to be attachable to and detachable from the suction cap 9 through a suction tube, not shown. Furthermore, the water-feeding tank 16 is attachable to and detachable from the air/water feeding mouthpiece 10 through an air/water feeding tube, not shown.

The ultrasound observation apparatus 14 controls various operations of the ultrasound endoscope 1, for example, controls driving of the ultrasound transducer 32 and performs operation for generating a video signal by performing signal processing on an electric signal obtained by driving control of the ultrasound transducer 32.

Note that the video signal generated in the ultrasound observation apparatus 14 is outputted to a display device, not shown. As a result, an ultrasound image is displayed on the screen of the display device which receives the video signal.

The insertion portion 2 of the ultrasound endoscope 1 includes, in a linked manner, in the following order from the distal end side: a distal end rigid portion 21; a bending portion 22 configured to be bendable in up/down direction and left/right direction, for example; and a flexible tube portion 23 which is long and has flexibility. Note that the above-described ultrasound transducer unit 30 is located on the more distal end side than the distal end rigid portion 21 and fixed to the distal end rigid portion 21.

The operation portion 3 is provided with bending operation knobs 25, 26 that perform bending operation of the bending portion 22. In addition, a treatment instrument insertion port 27, which introduces the treatment instrument into a body through a treatment instrument insertion conduit, not shown, provided in the insertion portion 2 and the operation portion 3, is provided to the operation portion 3 so as to be located at a position closer to the insertion portion 2.

The video processor 12 performs signal processing on the electric signal transmitted from an image pickup unit, not shown, provided in the distal end rigid portion 21, to thereby generate a standard video signal, and output the video signal to the display device, not shown, to display an endoscopic observation image on the screen of the display device.

If the ultrasound probe 50 according to the above-described first to fourth embodiments is applied to the ultrasound endoscope 1 thus configured, there is no need for increasing the length of the insulation pipe 36 in order to prevent the adhesive 52 from flowing out. Therefore, it is possible to form the distal end rigid portion 21, the length of which is short, which improves the operability.

In addition, since the adhesive 52 is prevented from flowing out, it is possible to surely prevent the bending of the bending portion 22 from being interfered with as a result that the adhesive 52 adheres to the region of the cable 41 located in the bending portion 22 and the adhered adhesive 52 is cured.

Note that description has been made above by taking the cases in which the ultrasound probe 50 is applied to the ultrasound endoscope 1 as examples. However, the ultrasound probe 50 may be provided in an instrument other than the ultrasound endoscope 1, and also in such a case, it is needless to say that it is possible to obtain the same effects as those in the case where the ultrasound probe 50 is applied to the ultrasound endoscope 1.

What is claimed is:

1. An ultrasound probe comprising:
an ultrasound transmission/reception portion having an ultrasound transmission/reception surface for transmitting and receiving ultrasound;
a cable having a distal end electrically connected to the ultrasound transmission/reception portion;
a housing configured to hold the ultrasound transmission/reception portion such that the ultrasound transmission/reception surface is exposed;
a hole portion provided to the housing and configured to lead out the cable from inside of the housing;
an insulation pipe through which the cable is inserted, the insulation pipe having a distal end side fixed to the hole portion in a state of contacting an inner circumference of the hole portion, and a proximal end side exposed outside the housing;
an insulation tube configured to cover an outer circumference of an exposed region of the insulation pipe which is exposed from the hole portion and an outer circumference of the cable led out from a proximal end of the insulation pipe;
an adhesive disposing area located from a distal end of the insulation tube for a predetermined distance between the outer circumference of the exposed region of the insulation pipe and an inner circumference of a distal end side region of the insulation tube covering the outer circumference of the exposed region;
an adhesive permeation preventing area located between the outer circumference of the exposed region of the insulation pipe and the inner circumference of the distal end side region of the insulation tube covering the outer circumference of the exposed region, at least a part of the adhesive permeation preventing area being located on a proximal end side with respect to the adhesive disposing area;
an adhesive located in the adhesive disposing area and configured to adhere the insulation pipe and the insulation tube to each other; and
a liquid dripping prevention portion disposed in the adhesive permeation preventing area between the outer circumference of the exposed region of the insulation pipe and the inner circumference of the distal end side region of the insulation tube, the liquid dripping prevention portion being configured to prevent the adhesive from flowing out from the proximal end of the insulation pipe and contacting the cable.

2. The ultrasound probe according to claim 1, wherein the liquid dripping prevention portion is a sticky member having a higher viscosity than the adhesive, the sticky member being configured to cling to the distal end side region of the insulation tube together with the adhesive, and located on a proximal end side with respect to the adhesive between the outer circumference of the exposed region of the insulation pipe and the inner circumference of the distal end side region of the insulation tube.

3. The ultrasound probe according to claim 1, wherein the liquid dripping prevention portion is a projection portion provided along an outer circumference of the proximal end of the insulation pipe and configured to block the adhesive flown out toward the proximal end side, the projection portion being located on a proximal end side with respect to the adhesive between the outer circumference of the exposed region of the insulation pipe and the inner circumference of the distal end side region of the insulation tube.

4. The ultrasound probe according to claim 3, wherein the projection portion is formed integrally with the insulation pipe by causing the outer circumference of the proximal end of the insulation pipe to be bulged.

5. The ultrasound probe according to claim 1, wherein the liquid dripping prevention portion is an absorbing member for absorbing the adhesive flown out toward the proximal end side, the absorbing member being located on a proximal end side with respect to the adhesive between the outer circumference of the exposed region of the insulation pipe and the inner circumference of the distal end side region of the insulation tube.

6. The ultrasound probe according to claim 1, wherein the liquid dripping prevention portion is a groove portion in which the adhesive is injected, the groove portion being formed on the outer circumference of the exposed region of the insulation pipe by causing the outer circumference to be dented.

7. The ultrasound probe according to claim 6, wherein the groove portion is formed in a circumferential shape on the outer circumference of the exposed region of the insulation pipe.

8. The ultrasound probe according to claim 1, wherein the liquid dripping prevention portion has a diameter larger than a diameter of the adhesive disposing area.

9. The ultrasound probe according to claim 8, wherein the liquid dripping prevention portion is extended to a proximal end of the insulation pipe.

\* \* \* \* \*